United States Patent [19]

Gordon et al.

[11] 4,425,923

[45] Jan. 17, 1984

[54] INCENTIVE SPIROMETER WITH AUTOMATIC LEVELLING

[75] Inventors: Marvin Gordon, East Winsor; Joseph Lichtenstein, Colonia, both of N.J.

[73] Assignee: Whitman Medical Corporation, Clark, N.J.

[21] Appl. No.: 324,379

[22] Filed: Nov. 23, 1981

[51] Int. Cl.³ .............................................. A61B 5/08
[52] U.S. Cl. ......................................... 28/727; 272/99
[58] Field of Search .............................. 128/725–727; 272/99; 73/861.55, 861.56, 861.57

[56] References Cited

U.S. PATENT DOCUMENTS

| | | | |
|---|---|---|---|
| 4,025,070 | 5/1977 | McGill et al. | 272/99 |
| 4,060,074 | 11/1977 | Russo | 272/99 X |
| 4,086,918 | 5/1978 | Russo | 272/99 X |
| 4,114,607 | 9/1978 | Russo | 272/99 X |
| 4,138,105 | 2/1979 | Hunger et al. | 272/99 |
| 4,170,228 | 10/1979 | Elson et al. | 128/725 |
| 4,182,347 | 1/1980 | Russo | 128/725 |
| 4,183,361 | 1/1980 | Russo | 128/725 |

*Primary Examiner*—Lee S. Cohen
*Assistant Examiner*—Christine A. Fukushima
*Attorney, Agent, or Firm*—Holman & Stern

[57] ABSTRACT

An incentive spirometer, of the type wherein an object is raised in a tube by a patient inhaling through the tube, is improved by automatically maintaining the tube vertically-oriented in spite of tilting of the frame from which the tube is supported.

11 Claims, 6 Drawing Figures

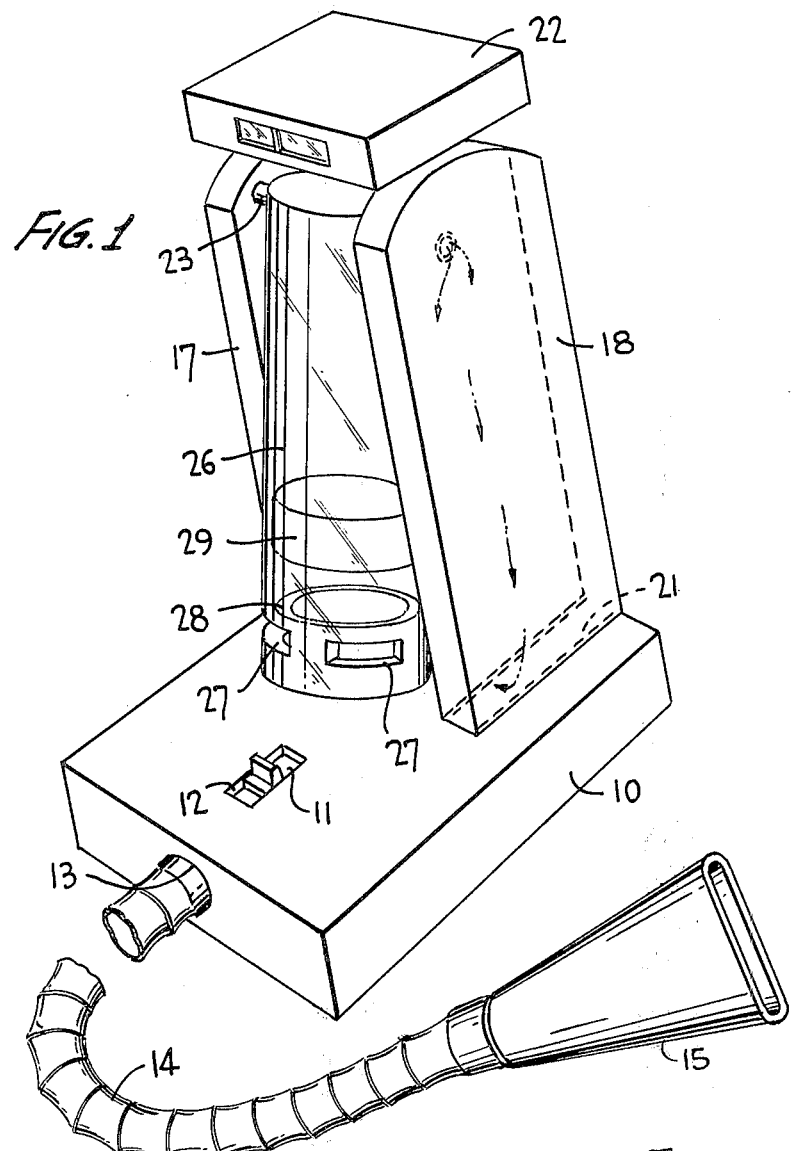
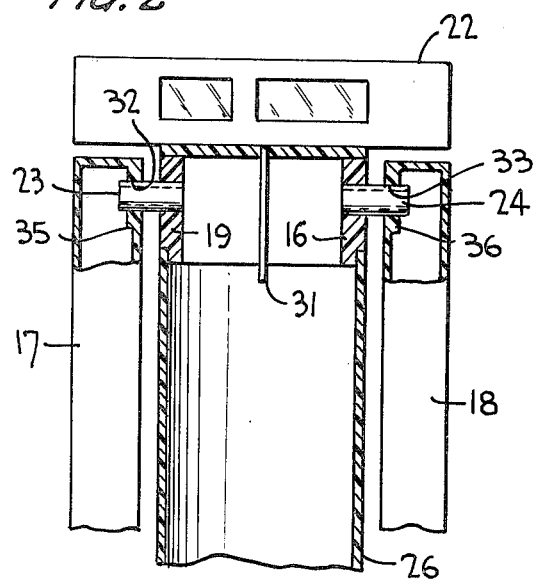
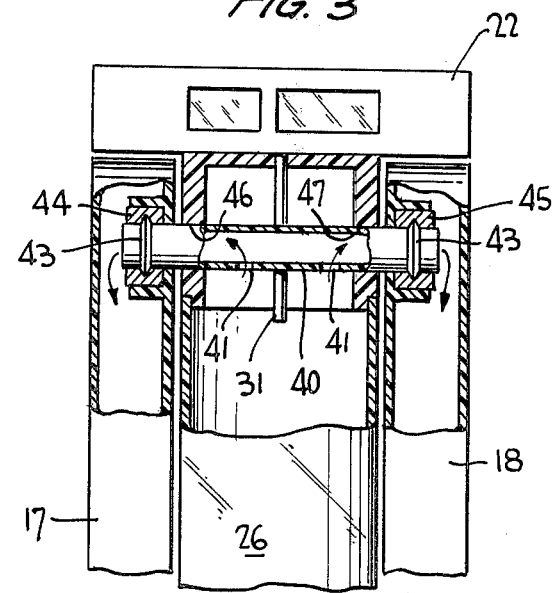

INCENTIVE SPIROMETER WITH AUTOMATIC LEVELLING

TECHNICAL FIELD

The present invention relates to therapeutic inhalation devices and, more particularly, to incentive spirometers having improved efficiency.

BACKGROUND OF THE INVENTION

The present invention relates to incentive spirometers of the type wherein an object is caused to rise in a transparent tube in response to inhalation through the tube by a patient. Incentive spirometers of this general type are well known in the prior art, as shown by U.S. Pat. Nos. 4,182,347; 4,183,361; 4,170,228; 4,114,607; 4,086,918; 4,025,070; and others. In addition, a prior art incentive spirometer of this type is illustrated and described in U.S. Patent Application Ser. No. 247,097, filed Mar. 24, 1981 now U.S. Pat. No. 4,391,283, by Edward N. Sharpless, Marvin Gordon and Joseph Lichtenstein, and bearing the title "Improved Incentive Spirometer", which patent application is expressly incorporated in its entirety herein by reference.

Incentive spirometers of this type have a common problem which results in an inaccuracy of the monitoring of the breathing exercise. Specifically, the tube in which the incentive member is caused to rise by inhalation should be maintained vertical so as to minimize frictional interaction between the incentive member and the inside wall of the tube. However, in use, it is common for the incentive spirometer to be placed next to the patient on a bed or other surface which is not necessarily level. When the supporting frame for the incentive spirometer tilts, the inhalation tube likewise tilts so that the desired vertical orientation is destroyed. Moreover, in some instances, the patient will support the frame in his or her hands and will inadvertently cause the frame to tilt with the same undesirable result.

SUMMARY OF THE INVENTION

It is therefore an object of the present invention to provide a method and apparatus for maintaining the inhalation tube of an incentive spirometer in a vertical orientation, irrespective of tilting of the frame which supports the inhalation tube.

In accordance with a first embodiment of the present invention, the inhalation flow tube is supported for movement about a horizontally-extending axis disposed through a portion of the flow tube located near its upper end. Two projections from the flow tube extend in diametrically opposite directions and are journaled in respective holes in the frame member. The projections serve as part of the flow passage to provide flow communication from the tube interior to a flow passage disposed within the frame.

In a second embodiment, the flow tube is suspended from the frame by means of a flexible cord or cable so that the vertical orientation of the flow tube will be achieved irrespective of the direction in which the frame is tilted.

BRIEF DESCRIPTION OF THE DRAWINGS

The above and still further objects, features, and advantages of the present invention will become apparent upon consideration of the following detailed description of specific embodiments thereof, especially when taken in conjunction with the accompanying drawings, wherein:

FIG. 1 is a view in perspective of a first embodiment of the present invention showing the frame tilted but with the air tube remaining vertical;

FIG. 2 is a front view in partial section showing the details of the pivot arrangment for the air tube with respect to the frame for the embodiment of FIG. 1;

FIG. 3 is a view similar to that of FIG. 2 for a second embodiment of the present invention;

DESCRIPTION OF THE PREFERRED EMBODIMENTS

Figure 4:
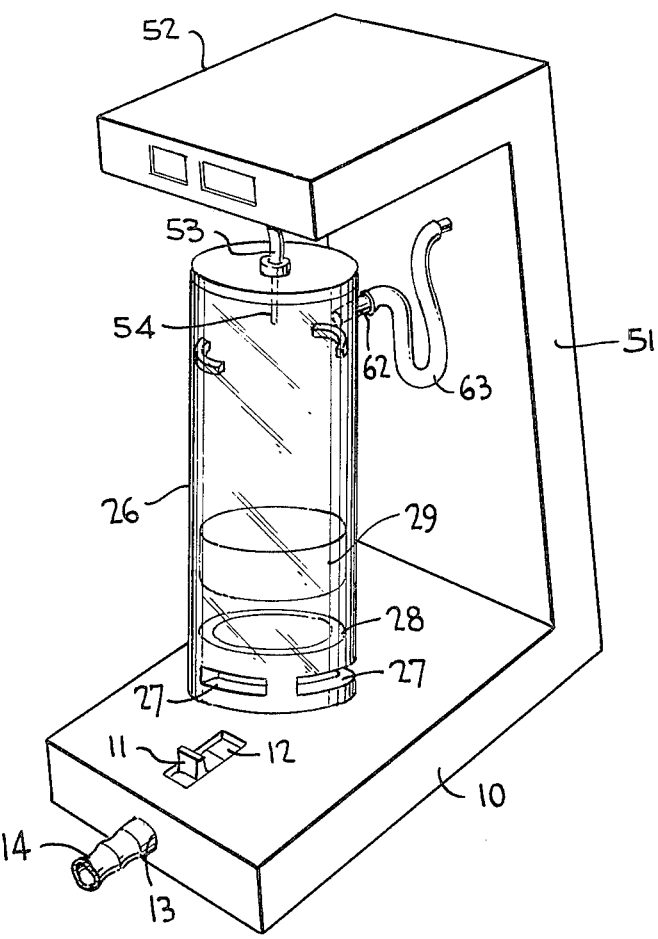
FIG. 4 is a view in perspective of still another incentive spirometer embodiment of the present invention.

Referring specifically to FIGS. 1 and 2 of the accompanying drawings, there is illustrated an incentive spirometer of the type wherein the incentive for the patient is visually perceived by the patient in the form of an object raised in a transparent tube as a function of the patient's inhalation efforts. The incentive spirometer of FIGS. 1 and 2 is conventional in all respects except for the provision of means to permit tilting of the transparent tube with respect to its support frame so that the tube can be maintained vertically oriented in spite of tilting of the support frame. The spirometer includes a base 10 which is in the form of a generally flat rectangular enclosure for a flow chamber. The top surface of base 10 is provided with an aperture 12 in which a valve 11 is slidably disposed in order to vary the portion of aperture 12 which is exposed to the ambient environment. In other words, valve 11 controls the size of the opening into the flow chamber via aperture 12. Another opening 13 into the flow chambers is defined in the front wall of base 10. A flexible hose 14 has one end connected to the flow chamber at opening 13 by means of a suitable fitting, clamp, or the like. The other end of hose 14 terminates in a mouth piece 15 adapted to be inserted into the mouth of a patient when the spirometer is in use.

A support frame takes the form of a pair of spaced vertically-extending legs 17 and 18 projecting upward from the top surface of base 10. Members 17 and 18 are hollow (or at least have flow passages vertically defined therein) and communicate with suitably provided openings 21 (only one visible in FIG. 1) in the top surface of base 10. In this manner, the interior of legs 17 and 18 are in flow communication with the flow chamber enclosed within base 10.

A transparent vertically-extending tube 26 is secured between the vertically-extending frame members 17 and 18. The bottom end of tube 26 is suspended above the top surface of base 10. Two diametrically-opposed stop members 19 and 16 are secured to the inside wall of tube 26 proximate the top of the tube. A pair of hollow cylindrical support members 23 and 24 are rigidly secured to and project radially outward from respective stop members 19 and 16. These pivotal support members 23 and 24 are received in suitable respective apertures 32 and 33 defined through the upper proximity of frame members 17 and 18, respectively. Molded apertured retainer ledges 35 and 36 are secured to the interior surface of frame members 17 and 18 so that their apertures align with the apertures 32 and 33. In this way, the ledges 35 and 36 serve as greater support for the pivotal support members 23 and 24. Pivotal support members 23 and 24 are hollow and provide flow communication from the interior of tube 26 to the interior of frame members 17 and 18, respectively. In order to protect against leakage of flow, suitable O-rings may be provided at the pivot connection between the support members (23, 24) and retainer ledges (35, 36).

A housing 22 for electronic circuitry (of the type described in the aforementioned U.S. Patent Application Ser. No. 247,097 now U.S. Pat. No. 4,391,283,) is secured to the closed top end of transparent tube 26 and extends laterally above the frame members 17 and 18. Housing member 22 includes an actuator switch 31 which projects downwardly into tube 26 to a level below stop members 19 and 16. The undersurface of housing 22 is provided with a suitable circular recess for receiving and rigidly engaging the upper end of tube 26 so that the housing member 22 is constrained to pivot with tube 26 about the common axis of support members 23 and 24. In this regard, the top edges of frame members 17 and 18 are rounded to present a convex upwardly-facing edge toward housing 22 so as not to interfere with the front-to-back pivoting of housing 22.

The lower end of tube 26 is provided with one or more angularly extending openings 27 to permit admission of air into the bottom of the tube. An annular flange 28 is disposed just above the openings 27 and extends radially inward to serve as a seat for an object 29 disposed in the tube. Object 29 serves as the incentive member which is raised in tube 26 as a function of the inhalation effort of the patient. The incentive member may take the form of the various elements described and illustrated in the aforementioned U.S. Patent Application Ser. No. 247,097 now U.S. Pat. No. 4,391,283, or may simply take the form of a spherical member as is conventional in other incentive spirometers.

It will be appreciated that, upon a suction being applied to mouthpiece 15, air from the ambient environment is drawn through a flow path including openings 27, tube 26, pivotal support members 23 and 24, the interiors of frame members 17 and 18, the flow chamber enclosed within base 10, and flexible tubing 14. Incentive member 29 is raised in tube 26, in a conventional manner, as a function of the inhalation effort exerted by the patient. Valve 11 serves to provide a parallel flow path for air from ambient to mouthpiece 15 so as to increase or decrease the effort required on the part of the patient to raise object 29. Specifically, if valve 11 is wide open, a stronger inhalation effort will be required on the part of the patient to raise object 29 since a considerable portion of the air inhaled by the patient will be shunted through aperture 12 rather than through the tube. As the opening of valve 11 is made smaller, a greater proportion of the inhaled air flows through tube 26, thereby requiring less effort by the patient to raise object 29. The various positions of valve 11 can be calibrated in flow rate required to achieve the incentive goal.

If the base member 10 is placed on a surface which is not level so that it tilts about any horizontal axis disposed perpendicular to the longitudinal axis of tube 26, the tube and housing 22 pivot with pivotal support members 23 and 24 so that the tube 26 remains vertical. Thus, if base 10 is placed alongside the patient on a bed with opening 13 facing the patient's body, the sag in the mattress produced by the weight of the patient will cause base 10 to tilt with its forward side down. Tube 26 and housing 22 pivot accordingly so that the bottom of tube 26 moves closer toward valve aperture 12. By maintaining tube 26 substantially vertical, the present invention minimizes frictional engagement between object 29 and the inside of the tube so that such frictional engagement has little or no effect on the incentive provided for the inhaling patient.

An alternative embodiment is provided in FIG. 3, differing only in the specific details of the pivotal mounting arrangement. Elements illustrated in FIG. 3 which have identical or similar counterparts in FIG. 1 are provided with the same reference numerals as that which appear in FIG. 1. The pivotal support members 23 and 24 which project in diametrically opposite directions from tube 26 in FIG. 1, are replaced in the FIG. 3 embodiment by a single tubular member 40 which extends through diametrically opposed openings 46 and 47 proximate the upper end of tube 26. Bushings 44 and 45 are concentrically disposed about tube 40 in the region of holes 46 and 47, and are snap-fitted over respective ferrules 43 molded integral with tube 40, so that tube 26 is free to pivot about the axis of tube 40 relative to the bushings 44 and 45 and the tube 40. The opposite extremities of tube 40 extend through openings 32 and 33 and are rigidly secured therein so that tube 40 is fixed relative to frame members 17 and 18. Tube 40 has openings 41 disposed therein and serves as a flow passage for air from tube 26 into the interiors of frame members 17 and 18. Housing 22 is secured atop tube 26 in the same manner described in relation to the embodiment of FIG. 1.

Figure 5:
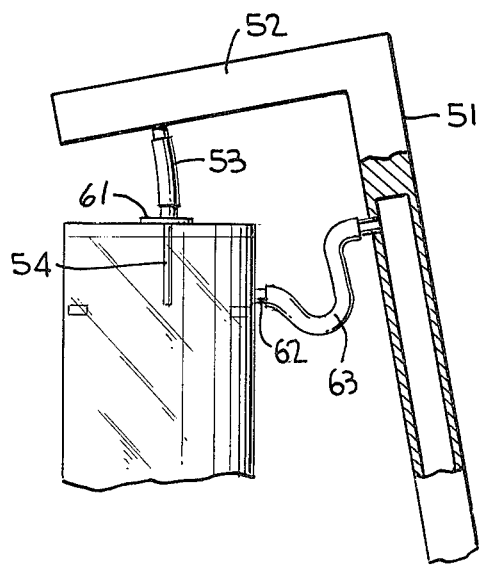
FIG. 5 is a broken side view in partial section of the embodiment of FIG. 4.
Figure 6:
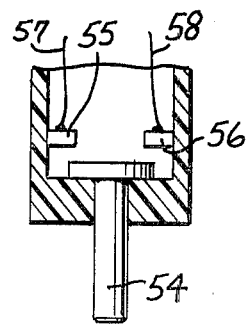
FIG. 6 is a detailed view in section of the support member for the air tube in the embodiment of FIGS. 4 and 5.

The embodiments of FIGS. 1 and 3 are arranged to provide self-levelling for the tube 26 in response to tilting of the base member in substantially only one direction. It is within the scope of the present invention to provide automatic vertical orientation of tube 26 irrespective of the direction of tilt of base member 10. An embodiment in which this universal correction is achieved is illustrated in FIGS. 4–6 to which specific reference is now made.

In a manner similar to the embodiments of FIGS. 1 and 2, a base 10 includes an aperture 12 in its top surface with a slide valve 11 disposed therein. The front wall of base 10 is provided with an aperture 13 from which a hose 14 extends to a mouthpiece (not shown). A transparent tube 26 is suspended over base 10 and includes angularly extending openings 27 above which an annular flange 28 is disposed to serve as a seat for incentive member 29. The remainder of the spirometer illustrated in FIGS. 4–6 differs however. Specifically, a frame member includes a single upstanding member 51 projecting upward from a rearward location of the top surface of base 10. A top frame portion 52 extends from member 51 in cantilever-like fashion over base 10 and spaced from base 10 by a difference somewhat greater than the length of tube 26. Frame portion 52 comprises the housing for the electronics circuitry which is housed in housing 22 in the embodiments of FIGS. 1 and 3. Frame member 51 has a hollow flow passage portion defined therein which communicates with the flow chamber defined interiorly of base 10. It should be noted that top frame portion 52 and frame member 51 may be formed integrally or as two separate and separable pieces. A flexible cable 53 extends downwardly from within frame portion 52 at a location near the distal end of that frame member. Cable 53 has, at its distal end, a switch member 54 projecting therefrom. Switch member 54, as best illustrated in FIG. 6, is movable axially within cable 53 when subjected to an externally-applied axial force. Switch member 54 includes a stem portion which projects from cable 53 and a head portion which is retained within cable 53 and serves to limit axial motion of the switch member when it abuts two terminals 55 and 56 secured at diametrically opposed locations within cable 53. Lead wires 57 and 58 extend from terminals 55 and 56, respectively, into the frame member 52 where it is employed as part of the circuitry housed therein. An annular nipple 61 projects from the top end of tube 26 and is adapted to receive the distal end of cable 53 in a friction fit. When the cable is thusly received within nipple 61, switch member 54 projects down into the tube so that it may be contacted by the incentive object 29 when that object is raised sufficiently by the inhalation efforts of the patient.

A further nipple 62 extends radially from tube 26 at a location proximate the upper end of the tube. Nipple 62 connects to a flexible flow tube 63 which is secure at its opposite ends to frame member 51 so as to provide flow communication between tube 26 and the interior of frame member 51.

Cable 53 is sufficiently flexible transversely so as to permit tube 26 to be suspended with a vertical orientation irrespective of the direction of tilt of base 10 and frame members 51 and 52. On the other hand, cable 53 should have sufficient longitudinal rigidity to permit insertion of the cable into nipple 61 in opposition to the frictional resistance presented by the nipple. Flow tube 63, on the other hand, is sufficiently flexible both transversely and longitudinally so as not to interfere with the automatic vertical orientation of tube 26 as the base and frame members tilt.

While we have described and illustrated specific embodiments of our invention, it will be clear that variations of the details of construction which are specifically illustrated and described may be resorted to without departing from the true spirit and scope of the invention as defined in the appended claims.

We claim:

1. An incentive spirometer comprising:
   an inhalation flow path through which air flows in response to an inhalation suction force applied thereto by a patient;
   a support frame;
   a hollow column disposed in said flow path and supported by said frame, said column having first and second ends;
   incentive means disposed in said column to move in opposition to gravity therein toward said second end in response to inhalation air flow through said column from said first end toward said second end; and
   levelling means for automatically maintaining said column in a substantially vertical orientation, with said second end being disposed above said first end, in response to tilting of said frame in at least one plane.

2. The incentive spirometer according to claim 1, wherein said levelling means comprises suspension means for suspending said column from said frame.

3. The incentive spirometer according to claim 2, wherein said suspension means comprises:
   a pair of generally cylindrical members extending co-axially in opposite horizontal directions from said column proximate said second end; and
   journal means for supporting said cylindrical members in said frame for rotation about their common axes.

4. The incentive spirometer according to claim 3, wherein said frame member includes a pair of hollow members comprising parts of said inhalation flow path, and wherein said pair of cylindrical members are hollow and provide flow communication from inside said column to said hollow members inside said frame.

5. The incentive spirometer according to claim 4, wherein said journal means includes a pair of annular bushings disposed in said frame for receiving said pair of cylindrical members, respectively, and snap-fit means for concentrically engaging said pair of bushings to said pair of cylindrical members, respectively.

6. The incentive spirometer according to claim 1, wherein said levelling means comprises means responsive to tilting of said frame in all directions from vertical for vertically orienting said column with said second end disposed above said first end.

7. The incentive spirometer according to claims 1 or 6, wherein said levelling means comprises an elongated flexible member suspended from said frame and having a distal end secured to said second end of said column.

8. The incentive spirometer according to claim 7, wherein said frame includes a housing for an indicator mechanism actuable by said incentive means and wherein said elongated flexible member is a cable having switch means disposed at said distal end and projecting into said second end of said column for selective actuation by said incentive means.

9. The incentive spirometer according to claims 3 or 6, wherein said column is transparent.

10. A method of minimizing friction between an incentive-indicating member and the walls of an inhalation flow path in which the member is translated by inhalation flow, said method comprising the step of automatically orienting said flow path in a vertical direction in response to tilting in at least one plane of a structure in which said flow path is supported.

11. An incentive spirometer comprising:
    inhalation flow path means for passing air therethrough in response to inhalation suction forces applied thereto by a patient;
    a support structure;
    a hollow column disposed in said flow path means and supported by said structure, said column having first and second ends;
    incentive indication means disposed in said column to move in opposition to gravity therein toward said second end in response to inhalation air flow through said column from said first end toward said second end; and
    levelling means for automatically maintaining said column in a substantially vertical orientation, with said second end being disposed above said first end, in response to tilting of said support structure in at least one plane, said levelling means comprising a means for suspending said column from said structure.

* * * * *